United States Patent
Darby et al.

(10) Patent No.: US 9,681,992 B2
(45) Date of Patent: Jun. 20, 2017

(54) WOUND CARE DEVICE

(71) Applicant: Medtrade Products Limited, Crewe, Cheshire (GB)

(72) Inventors: Stuart Darby, Trenthan (GB); Craig Hardy, Audlem (GB); Andrew Hoggarth, Wistaston (GB)

(73) Assignee: Medtrade Products Limited (GB)

( * ) Notice: Subject to any disclaimer, the term of this patent is extended or adjusted under 35 U.S.C. 154(b) by 0 days.

(21) Appl. No.: 14/441,282

(22) PCT Filed: Nov. 7, 2013

(86) PCT No.: PCT/GB2013/052925
§ 371 (c)(1),
(2) Date: May 7, 2015

(87) PCT Pub. No.: WO2014/072721
PCT Pub. Date: May 15, 2014

(65) Prior Publication Data
US 2015/0297414 A1    Oct. 22, 2015

(30) Foreign Application Priority Data

Nov. 7, 2012  (GB) .................................. 1220076.2

(51) Int. Cl.
*A61F 13/02* (2006.01)
*A61L 2/20* (2006.01)
(Continued)

(52) U.S. Cl.
CPC ...... *A61F 13/0213* (2013.01); *A61F 13/0283* (2013.01); *A61L 2/206* (2013.01);
(Continued)

(58) Field of Classification Search
CPC ........ C08L 5/08; A61L 15/28; A61L 26/0023; A61L 15/225; A61L 15/60;
(Continued)

(56) References Cited

U.S. PATENT DOCUMENTS 5,472,702 A    12/1995    Muth et al.
6,998,509 B1   2/2006     Nielsen
(Continued)

FOREIGN PATENT DOCUMENTS

| GB | 2488915 | 9/2012 |
|---|---|---|
| WO | 2009043839 | 4/2009 |
| WO | 2010031995 | 3/2010 |

OTHER PUBLICATIONS

ISA for corresponding Int'l Pat Appl. No. PCT/GB2013/052925, dated Feb. 19, 2014, 3 pages.

*Primary Examiner* — Aradhana Sasan
(74) *Attorney, Agent, or Firm* — Tarolli, Sundheim, Covell & Tummino LLP

(57) ABSTRACT

The present invention relates to a wound care device, and more specifically to an absorbent wound care device and a method for making the same. The wound care device is obtainable by bringing together a first material and an acidic substance to form an intermediate device, which first material does not substantially gel when exposed to a fluid but does gel when brought together with an acidic substance and exposed to a fluid, and exposing the intermediate device to ethylene oxide.

8 Claims, 2 Drawing Sheets

(51) Int. Cl.
  *A61L 15/22*   (2006.01)
  *A61L 26/00*   (2006.01)
  *A61L 15/60*   (2006.01)
  *A61L 15/28*   (2006.01)

(52) U.S. Cl.
  CPC ............. *A61L 15/225* (2013.01); *A61L 15/28* (2013.01); *A61L 15/60* (2013.01); *A61L 26/008* (2013.01); *A61L 26/0023* (2013.01); *A61L 2400/04* (2013.01)

(58) Field of Classification Search
  CPC .... A61L 2400/04; A61L 26/008; A61L 2/206; A61L 13/0213; A61L 13/0283
  See application file for complete search history.

(56) References Cited

U.S. PATENT DOCUMENTS

| | | |
|---|---|---|
| 2003/0049480 A1 | 3/2003 | Gagliardini et al. |
| 2005/0058694 A1 | 3/2005 | Nielsen |
| 2005/0203058 A1 | 9/2005 | Johnson |

WOUND CARE DEVICE

TECHNICAL FIELD

The present invention relates to a wound care device, and more specifically to an absorbent wound care device and a method for making the same.

BACKGROUND

There are many circumstances in which animals, both human and non-human, may become injured or wounded causing discharge of bodily fluids. When treating wounds which are exuding blood and other bodily fluids, it is advantageous to have an absorbent dressing which is capable of adapting to the conformation of any individual wound. Such dressings may be obtained by using fibre dressings or hydrogels. Fibrous wound dressings often present problems in terms of insufficient absorption of the bodily fluids, and/or they may suffer from a lack of cohesion, which may result in the dressing not being able to be removed from a wound in one piece.

Gel-based dressings have the benefit of being cohesive so that they do not stick to a wound site, making it possible to remove the dressing from the wound in one piece while providing an ideal moisture environment for wound healing. Additionally, they can have a low adherence to a wound site, allowing them to be removed from a wound easily without causing pain for the wounded party.

Wound care devices such as absorbent dressings comprising fibres which can gel are known in the art. U.S. Pat. No. 6,998,509 describes a wound care device which comprises chitosan fibres, which are capable of absorbing liquid to form a swollen coherent gel. The chitosan fibres are normally insoluble, non-swelling and non-gelling and so are treated with an acid and heat to convert them into an insoluble, water-swelling and water-gelling form. A similar wound care device is also detailed in US2005/0058694. Such dressings employing the use of gels effectively serve to entrap the absorbed fluids.

It would be advantageous to improve the absorbency of fibre dressings and to maintain that absorbency over the wear time of the dressing.

SUMMARY

Thus, it is an object of the present invention to provide a wound care device having improved absorbency and an improved structural integrity over wear time.

According to a first aspect of the present invention, there is provided a wound care device obtainable by bringing together a first material and an acidic substance to form an intermediate device, which first material does not substantially gel when exposed to a fluid but does gel when brought together with an acidic substance and exposed to a fluid, and exposing the intermediate device to ethylene oxide.

Typically, the fluid is a water-containing fluid. The fluid can be water, saline, wound exudates, blood or combinations thereof.

The wound care device of the present invention demonstrates increased absorbency, making it more adept to absorb fluids that a wound care device would typically come into contact with when used on a physiological target site, e.g. water, saline, wound exudates, blood. Thus, the exposure of the intermediate device to ethylene oxide has the dual purpose of providing a wound care device that is both sterile and shows increased absorbency and structural integrity over wear time.

The wound care device may be suitable for use on a physiological target site in or on the body of an animal. The animal may be a human or a non-human animal. The physiological target site may be a wound or it may be an opening in a body caused during a medical procedure, for example during surgery. Hereinafter, the physiological target site is referred to as a wound for illustrative purposes.

Typically, the first material and the acidic substance of the intermediate device do not react with each prior to exposing the intermediate device to ethylene oxide.

Preferably, neither the first material nor the acidic substance undergoes a chemical change to create a new compound when they are brought together to form the intermediate device. The intermediate device may therefore comprise a first material and an acidic substance, wherein the first material and acidic substance have not chemically reacted with each other or are not chemically linked. The term chemically linked would be well-known to a person skilled in the art as referring to two atoms or chemical moieties bonded together via a covalent, ionic or hydrogen bond.

In such embodiments, the intermediate device comprising an unreacted combination of the first material and the acidic substance is exposed to ethylene oxide.

As described in more detail herein, the first material and the acidic substance may only react with each other on exposure to fluid, such as wound fluid.

The present invention thus provides a wound care device obtainable by bringing together a first material and an acidic substance to form an intermediate device, which first material does not substantially gel when exposed to a fluid but does gel when brought together with an acidic substance and exposed to a fluid, and exposing the intermediate device to ethylene oxide, wherein the first material and the acidic substance of the intermediate device do not react with each other prior to exposing the intermediate device to ethylene oxide.

Particularly good results have been observed in exposing the intermediate device to ethylene oxide before the first material has reacted with the acidic substance. It has been observed that exposing the intermediate device to ethylene oxide before the first material and the acidic substance have reacted improves the fluid absorbency and fluid retention of the wound care device in use compared to wound care devices in which the one or more components have reacted and the reaction product has been sterilised with ethylene oxide, gamma radiation or the like.

The term 'acidic substance' is used herein to refer to a substance having a pH of less than 7.

The first material may comprise the first material as described in WO2010/031995, the contents of which are incorporated herein by reference.

Thus, individually the first material substantially does not gel when exposed to a fluid. It is only when it is brought together with an acidic substance in the wound care device of the invention and the combination is exposed to a fluid, such as water, saline, wound exudates or blood, i.e. fluids that the wound care device would usually come into contact with when being used on a physiological target site, that any gelling occurs.

The first material may be in the form of fibres, particles, granules, flakes, powder, or a combination of two or more of the aforesaid. Preferably, the first material is in the form of fibres.

The first material typically comprises an absorbent polymer such as chitosan, a partially de-acetylated chitin and/or a chitosan derivative, and will not substantially gel on its own when exposed to fluids. Any non-gelling chitosan or chitin salt or any blend of chitosan and/or chitin and their salts may be used so long as the combination of substances used for the first material does not substantially gel when exposed to fluids. An amount of a soluble (still non-gelling) chitosan salt could be advantageous so long as the combination does not gel when exposed to fluids.

Typically, the molecular weight of chitosan used for the preparation of the wound care device according to the present invention is less than about 2000000 more typically less than about 1000000, and even more typically less than about 500000, and most typically less than about 175000.

Chitosan fibres suitable for use as the first material in accordance with the invention are typically fibres with a deacetylation degree above about 50%, more typically above about 75% and most typically above about 85%.

Typically, the fibres have a minimum average length of about 3 mm and a maximum length of about 150 mm, more typically no more than about 76 mm. The preferred proportion between length and diameter of the fibres is at least 25; more preferred at least 80 and most preferred at least 500.

The fibrous structure of the chitosan may provide an essential coherence for use in a wound dressing. When used as e.g. a wound contacting fabric, it is important that the absorbent material is coherent, thus rendering it possible to remove the wound dressing in one piece from the wound.

The acidic substance may comprise one or more acids.

The one or more acids are generally organic acids, although inorganic acids may also be used. Examples of acids which could be used in accordance with the invention include, but are not limited to, formic, acetic, halogen acetic acids (such as fluoro- or chloroacetic acids), ascorbic, hydrochloric, sulphuric, propanoic, propenoic, lactic, succinic, acrylic, glyoxylic, pyruvic or a hydroxy propionic/butanoic acid.

Typically, the one or more acids are selected from lactic, acetic and succinic acids. More typically, the acid used comprises lactic and/or acetic acids and most typically the acid is lactic acid. The use of an acid which is already present in the body could be an advantage in some potential indications.

The first material may be partially or completely coated with the acidic substance.

When the wound care device is placed on a surface of a body which has fluids associated therewith (typically a wound site on a human or animal body), the fluid causes the acidic substance to react with the first material, which typically contains chitosan or partially de-acetylated chitin. In such embodiments, the reaction forms the corresponding salt of the chitosan or partially de-acetylated chitin. The acidic substance is typically at least partially soluble in the fluid to aid transmission.

For example, a chitosan salt is prepared in situ when an appropriate acid comes into contact with the chitosan. It will be appreciated that the acid may be any inorganic or organic acid which yields a chitosan salt.

The reaction with the acidic substance may convert the first material from a non-swelling, non-gelling material to a swellable, gellable material, but one which is still substantially water insoluble. Once the converted first material comes into contact with the fluid from the wound site it gels in situ, effectively encapsulating the fluid.

The first material is preferably chitosan. Although chitosan is typically insoluble, it is also possible for the chitosan to be at least partially or completely dissolved in the presence of the acidic substance, if desired. If a soluble chitosan salt is required, the acidic substance used to react with the chitosan must be one which yields a salt which is soluble in bodily fluids. Appropriate acidic substances or combination of acidic substances for yielding a soluble chitosan salt will be apparent to a skilled person. For example, chitosan phosphate is substantially insoluble in water, and so use of phosphoric acid alone would hence be less suitable as the acidic substance for this purpose. Therefore, a portion of the chitosan for use with the present invention can be first converted into a water soluble salt so that it is soluble in blood and can act as a haemostat to form a gel/clot with the blood to stem blood flow.

Chitosan can act as a haemostat in two ways; either by gelling with water in the blood and bonding to wet tissue to plug a wound, or by dissolving and bonding with the surface of red blood cells to create a clot-like gel. The properties of the combinations of chitosan and acidic substance are dependent upon the nature of the chitosan (e.g. molecular weight and degree of deacetylation), as well as the particular acid used and the quantities present.

The presence of the acidic substance removes the need to pre-treat the first material with an acid. Carboxymethyl cellulose fibre used in existing wound care devices requires the treatment of cellulose fibre with toxic acids in a volatile solvent.

Additionally or alternatively to coating the first material with the acidic substance, the acidic substance may be associated with a second material. The second material may act as a carrier material for the acidic substance. The second material may also add to the structural integrity of the wound care device.

Thus, there is also provided a wound care device obtainable by bringing together a first material and a second material having an acidic substance associated therewith to form an intermediate device, which materials individually do not substantially gel when exposed to a fluid but do gel when brought together and exposed to a fluid, and exposing the intermediate device to ethylene oxide.

Typically, the second material and the acidic substance do not react with each other prior to exposing the intermediate device to ethylene oxide.

The second material may be different to the first material.

The second material may have the acidic substance absorbed therein.

The second material may not substantially gel on its own when exposed to fluids. The second material may comprise any one or more of the second materials as described in WO2010/031995.

The second material may be any non-gelling material. Such a material should be able to absorb or act as a carrier for the acidic substance without permanent bonding occurring. Thus, it is preferable that neither the second material nor the first material react with the acidic substance when brought together to form an intermediate device, which is then exposed to ethylene oxide. Typical materials include but are not limited to polymers such as cellulose, cellulose derivatives (e.g. ethyl cellulose, methyl cellulose, etc.), cotton, alginate, viscose, polypropylene, polyethylene or any combination of such materials.

In some embodiments, the first and second materials may be mixed together or may be segregated in separate layers or sections of the device. The resulting gelling pad could be used as a component in a wound dressing construction, for example, as the absorbent part of a more complicated structure with alternative backing, adhesive or wound contact materials.

The backing may comprise medical grade sheet materials such as but not limited to polymer films, thin foams and fabrics e.g. polyurethane films, polyurethane foams, nonwoven fabrics, etc.

Suitable skin contact adhesives may include, but are not limited to, acrylate, silicone, or polyurethane based adhesives. They can be based on hydrogels and can be porous to moisture with a high moisture vapour transmission rate. They can be applied from water emulsions, solvents or using hot melt systems. The adhesives should have a good skin tack but give minimal skin trauma on removal. They can constitute 100% coverage of the backing, or a partial coverage thereof in the form of a pattern or mesh.

The wound contact materials can include, but are not limited to, non-adherent layers which give very low or no adhesion to skin, wicking layers to speed up the absorption of fluid, active carrier layers for delivery of a therapeutic material (such as a pharmaceutical, haemostat, antimicrobial, wound healing agent, or scar reducing agent) and adhesive layers to help in holding the dressing in place while potentially reducing trauma on removal. They can be based on a polymer mesh, a fabric (e.g. nonwoven), and a hydrogel adhesive or partial adhesive coverings.

One or more of the materials may be fibrous, and the first and second materials may comprise a fibrous wound dressing.

The first and second materials may be combined together such that the intermediate device forms a nonwoven fabric. The first and second materials may typically be carded or needled together.

Furthermore, all the fibres in the wound care device of the invention may not individually gel if they are kept separate from each other.

It has been observed that the performance parameters of a wound care device as described herein are affected by the sterilisation technique used during manufacture. In this regard, it has been observed that a wound care device as described herein that has been exposed to ethylene oxide demonstrates improved absorbency compared to the same devices that are non-sterilised or sterilised by techniques other than ethylene oxide, such as exposure to gamma radiation.

It has further been discovered that the aforementioned effect applies both to wound care devices comprising a first material and an acidic substance and to wound care devices comprising a first material as described herein and a second material as described herein having an acidic substance associated therewith.

The effect described above is particularly apparent when the intermediate device comprising the first material, optional second material, and the acidic substance is exposed to ethylene oxide before the first material and/or second material has reacted with the acidic substance.

The term 'intermediate device' can comprise either a first material and an acidic substance or a first material and an acidic substance, wherein the acidic substance is associated with a second material as described herein.

The exposure of the intermediate device to ethylene oxide may comprise a sterilisation phase.

The sterilisation phase may comprise exposing the intermediate device to gaseous ethylene oxide. The sterilisation phase may be conducted in a chamber. The chamber is preferably sealed.

The concentration of ethylene oxide should be sufficient to sterilise the intermediate device. The concentration of ethylene oxide in the sterilisation phase may be from 250 to 900 mg/l, preferably from 450 to 700 mg/l, more preferably from 500 to 700 mg/l and most preferably from 550 to 650 mg/l. Good results have been observed with a concentration of ethylene oxide of around 565 to 635 mg/l.

The duration of the sterilisation phase may vary depending on the nature of the intermediate device and whether it is packaged prior to sterilisation. These factors can affect the passage of ethylene oxide through the product and hence affect the duration of sterilisation. The duration of the sterilisation phase should be sufficient to ensure that the intermediate device is sterilised. Typically, the duration of the sterilisation phase may be from 0.5 to 12 hours, preferably from 1 to 5 hours and most preferably from 1 to 3 hours. Good results have been observed at around 2 hours.

The sterilisation phase may be conducted in a sterilisation chamber under a reduced pressure. Preferably, the sterilisation chamber is under vacuum. The pressure inside the sterilisation chamber may range from 200 to 1000 mbar, preferably from 300 to 600 mbar and most preferably from 342 to 384 mbar. Good results have been observed under a pressure of around 360 to 370 mbar, such as for example 366 mbar.

The sterilisation phase may be conducted at a temperature of from 30 to 60° C., preferably from 45 to 55° C. Good results have been observed when the sterilisation phase is conducted at around 50° C.

The chamber may undergo preparation steps prior to the injection of gaseous ethylene oxide. Such preparation steps may comprise any one or more of the following: a vacuum of the chamber, a leak test, injection and subsequent evacuation of an inert gas such as nitrogen, and steam injection and dwelling.

In some embodiments, the intermediate device may undergo a pre-sterilisation phase prior to the sterilisation phase. The pre-sterilisation phase is intended to raise the core temperature of the intermediate device prior to exposure to ethylene oxide in the sterilisation phase. Typically, the pre-sterilisation phase comprises the step of subjecting the intermediate device to a temperature in the region of 35 to 55° C. and a relative humidity of from 45 to 75% for around 10 to 12 hours.

Once the pre-sterilisation phase is complete, the intermediate device may be moved into the chamber for the sterilisation phase described hereinbefore.

In some embodiments, the intermediate device may undergo a post-sterilisation phase that proceeds the sterilisation phase.

The post-sterilisation phase is intended to remove ethylene oxide gas used in the sterilisation phase. The post-sterilisation phase may therefore be referred to as a 'de-gas' phase.

The post-sterilisation phase may comprise the removal of gases under vacuum.

The post-sterilisation phase may additionally or alternatively comprise one or more wash steps. A wash step typically involves a circulation of air or an inert gas through the interior of the chamber and/or the contents therein. The inert gas is not limited to a specific gas and may comprise any gas or mixture of gases that does not react with the contents of the chamber. Suitable inert gases may include noble gases, such as argon, and/or nitrogen. Preferably, the inert gas is nitrogen.

In some embodiments, the post-sterilisation phase comprises sequential wash and vacuum steps. The post-sterilisation phase may comprise one or more washes and additionally or alternatively one or more vacuum steps. The one or more washes and vacuum steps may be performed in any order.

The post-sterilisation phase may be conducted at the same or a reduced temperature as the sterilisation and/or pre-sterilisation phases. Preferably, the post-sterilisation phase is conducted at a temperature in the range 25 to 60° C., more preferably in the range 25 to 55° C. and most preferably at a temperature in the range 30 to 50° C.

The post-sterilisation phase should be conducted for a length of time suitable to ensure that sufficient residual ethylene oxide is removed from the intermediate device. The duration of the post-sterilisation phase may vary depending on the nature of the intermediate device.

Some methods may comprise a pre-sterilisation phase and a sterilisation phase; some methods may comprise a sterilisation phase and a post-sterilisation phase; and some methods may comprise a pre-sterilisation phase, a sterilisation phase and a post-sterilisation phase.

Further components which may be added to the wound care device include but are not limited to wetting agents such as surfactants, colouring agents, adhesives to give the fabric a sticky texture, processing aids, inert materials, bulking agents, absorbent polymers, antimicrobials and meltable agents to help the fabric stick together.

The wound care device of the invention removes the need for using volatile solvents, reduces pollution and risk of exposure to hazardous materials for workers, as well as providing a less expensive and easier process to carry out. The waste materials which are produced are cheaper to process and are more environmentally friendly. Additionally, some actives are easy to apply in a water base, so new and different materials can be easily incorporated.

The wound care device may include one or more wound healing agents, one or more antimicrobial agents, such as silver, silver salts, silver-containing compounds, fibres containing silver, chlorhexidine, etc; growth factors; cytokines; agents which absorb agents which delay healing such as MMP's (matrix metalloproteinase's) and elastase, and/or haemostats. The active agent could be presented on the first material, the second material if present, or on a third material.

In another embodiment, surfactants could be used to help the wetting out of the wound care device, and or inert materials could be included either to help the wetting out, or to add strength or bulk. Typical levels of any of these components could be from ppm levels up to about 50%. More typical levels would be less than about 10%, still more typically less than about 5%.

The wound care device of the present invention may be used as part of a haemostatic material, and could comprise one or more further haemostats other than those described herein. Such further haemostats may comprise a polysaccharide or a mineral such as clay or kaolin. By "haemostat", it is meant any agent which is capable of producing a clot or plug which stops or reduces bleeding when it comes into contact with blood.

In some embodiments, chitosan is at least partially dissolved by the acidic substance and/or the fluid from the physiological target site and is absorbed into the body. The presence of the haemostat in the bodily fluid causes the e.g. blood to clot more quickly and stems the blood flow.

Chitosan salts are ideally suited for the applications described herein as chitosan is readily broken down in the body. Chitosan is converted to glucosamine by the enzyme lysozyme and is therefore excreted from the body naturally. It is not necessary to take any measures to remove the chitosan from the body; however, it can be removed if desired. Furthermore, chitosan salts exhibit mild antibacterial properties and as such their use reduces the risk of infection.

The viscosity of the chitosan used according to the invention may typically be less than about 1000 cP, more typically less than about 500, even more typically less than about 300. Advantageously, the viscosity is from about 40 to about 200 cps.

Other haemostats which could be used include, but are not limited to, calcium, vitamin K, fibrinogen, thrombin, factor VII, factor VIII, clays such as kaolin, oxidised regenerated cellulose, gelatin, or collagen, etc.

By the terms "water-swelling", "water-gelling" and "substantially water-insoluble" is meant that when the fibres are contacted with a fluid, such as water, saline, wound exudates or blood, they will absorb the fluid and swell by forming a gel, and will not substantially dissolve.

The wound care device of the invention may take any suitable form and may be provided in a range of different sizes, shapes and thicknesses necessary to deal with a wound, such as square, rectangular, circular or elliptical. For example, the device may be a generally flat shape with little height relative to its width/depth. Any regular or irregular shape may be employed. It may be provided in large sheets which can be cut to the required size.

The thickness of the device may be varied between upper and lower limits as desired. The upper limit of the thickness is typically about 5 cm, down to a few microns, such as 5-10 microns. It is however preferable that the device is flexible so that it can be curved to fit the contours of the body.

The chitosan typically has a pH of from about 6.0 to about 8.0. Chitosan salts can have a pH from about 3.5 to about 8.0. The pH is largely dependent upon the particular chitosan or chitosan salt used, as they each have a different pH.

Whilst the wound care device has been described hereinbefore as comprising one or two materials, there may be more materials if desired, such as three, four, five, or six different materials. Non-limiting examples of materials which could be used include materials to speed up or slow down the availability of the acidic substance, or any materials which would not affect the gelling but would add wet/dry strength, such as another already complete nonwoven fabric, a polymer net, a knitted fabric or strong fibres or adhesive/cohesive agents to hold the fabric together.

According to a second aspect of the present invention, there is provided a method of sterilising a wound care device, comprising the steps of (a) bringing together a first material and an acidic substance to form an intermediate device, which first material does not substantially gel when exposed to a fluid but does gel when brought together with an acidic substance and exposed to a fluid, and (b) exposing the intermediate device to ethylene oxide.

According to a further aspect of the invention, there is provided a use of a wound care device as described herein in absorbing a discharge of a bodily fluid from a physiological target site.

According to a further aspect of the invention, there is provided a wound care device as described herein for use in absorbing a discharge of a bodily fluid from a physiological target site.

The features of the second and further aspects of the present invention may comprise any of the features of the first aspect of the present invention as desired or as appropriate.

BRIEF DESCRIPTION OF THE DRAWINGS

The invention will now be described further by way of example with reference to the following drawings which are intended to be illustrative only and in no way limiting upon the scope of the invention.

DETAILED DESCRIPTION

Figure 1:
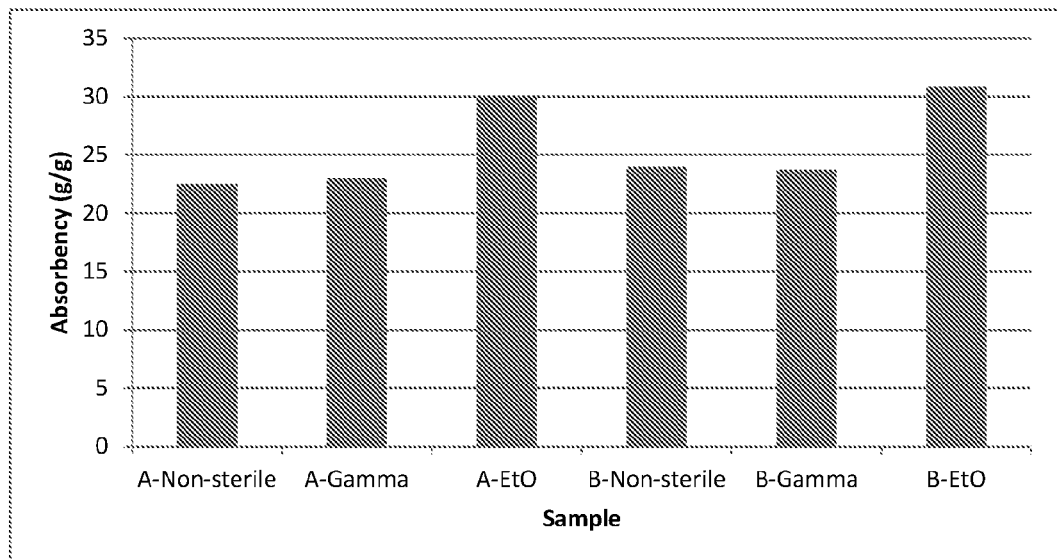
FIG. 1: is a graphical representation showing change in absorbency of a sample wound care device exposed to different sterilisation methods.

The following specific examples of the present invention compare the absorbency of four sample wound care devices following exposure to ethylene oxide in accordance with the present invention, gamma irradiation and no sterilisation.

In the preparation of Samples A and B below, the lactic acid was coated onto a first material of chitosan fibres. In Samples C and D, the lactic acid was coated onto a second material of cellulose fibres, with the first material of chitosan fibres being uncoated. In Samples A to D, the acidic substance does not react with the chitosan fibres, or the cellulose fibres, before exposure to ethylene oxide, or gamma radiation.

The process of coating the fibres with the acid typically comprises mixing the fibres with a solvent, typically a non-aqueous solvent, adding the acid to the mixture and then removing the solvent, typically by flashing off the solvent.

Preparation of Sample A:

1.7 dtex chitosan staple fibres were carded and needled to make a non-woven fabric. Lactic acid was added to the chitosan fabric to give a concentration of 20% w/w.

Preparation of Sample B:

1.7 dtex chitosan staple fibres were carded and needled to make a non-woven fabric. Lactic acid was added to the chitosan fabric to give a concentration of 55% w/w.

Samples C and D were prepared in accordance with the methods described in WO2010/031995.

Preparation of Sample C 2.4 dtex cellulose staple fibres (Lenzig, Austria) were manufactured. Lactic acid was added to the cellulose fibres to give a concentration of 25% w/w.

The resulting fibres were blended with 1.7 dtex chitosan staple fibres in a ratio of 55:45 chitosan to cellulose (coated with lactic acid). The combined fibres were carded and needled to make a non-woven fabric.

Preparation of Sample D 2.4 dtex cellulose staple fibres (Lenzig, Austria) were manufactured. Lactic acid was added to the cellulose fibres to give a concentration of 30% w/w. The resulting fibres were blended with 1.7 dtex chitosan staple fibres in a ratio of 55:45 chitosan to cellulose (coated with lactic acid). The combined fibres were carded and needled to make a non-woven fabric.

The compositions of Samples C and D are shown in Table 1.

TABLE 1

Compositions of Samples C and D

| SAMPLE | Cellulose Acid content | Cellulose carrier | Blend ratio Cellulose:Chitosan | GSM of 1 layer | No. of layers carded together | Total gsm |
|---|---|---|---|---|---|---|
| C | 25% | None | 45:55 | 135 | 1 | 135 |
| D | 30% | None | 45:55 | 135 | 1 | 135 |

Exposure to Ethylene Oxide

Portions of non-woven fabric prepared in Samples A to D were each separately exposed to ethylene oxide in a chamber following the processing cycle (SynergyHealth-Soft Mixed Cycle) shown in Table 2 to provide inventive samples A-EtO, B-EtO, C-EtO and D-EtO according to the present invention.

TABLE 2

Example cycle for exposure to Ethylene Oxide

| Step | Chamber Activity | Time (mins) | Pressure (mbar) | Temp. |
|---|---|---|---|---|
| 1 | Vacuum | 20-50 | 68 | |
| 2 | Leak test | 5-10 | — | |
| 3 | Nitrogen injection | 10-30 | 400 | |
| 4 | Re-evacuation | 15-40 | 68 | |
| 5 | Steam injection | >0, ≤10 | 42 | |
| 6 | Steam dwell | 30-50 | | 50 |
| 7 | Ethylene Oxide gas injection | 5-60 | 366 | 50 |
| 8 | 1$^{st}$ post-exposure vacuum | 20-60 | 68 | |
| 9 | Wash 1 - Nitrogen | 20-40 | 876 | |
| 10 | 2$^{nd}$ post-exposure vacuum | 20-40 | 68 | |
| 11 | Wash 2 - Nitrogen | 20-40 | 876 | |
| 12 | 3$^{rd}$ post-exposure vacuum | 20-40 | 68 | |
| 13 | Air wash x8 | 10-40 | 600 | |
| 14 | Post-exposure vacuum 4-11 | 10-40 | 200 | |
| 15 | Final air admission | 15-60 | 1000 | |

Comparative Exposure to Gamma Irradiation

Portions of non-woven fabric prepared in Samples A to D were each separately exposed to gamma irradiation (25-35 kGrays) in accordance with methods known in the art to provide comparative samples A-Gamma, B-Gamma, C-Gamma and D-Gamma.

For further comparative analysis, non-sterilised portions of Samples A to D, namely, A-Non-sterile, B-Non-sterile, C-Non-sterile and D-Non-sterile, were also tested.

Absorbency Testing

A test solution, comprising sodium/calcium chloride containing 142 mmol/liter of sodium ions and 2.5 mmol/liter of calcium ions, was prepared to mimic serum and wound fluid.

Test 1:

A known area of samples 'A-EtO', 'A-Gamma', 'A-Non-sterile', 'B-EtO', B-Gamma', and 'B-Non-sterile' was weighed (dry weight) and submerged in the test solution for 30 minutes. The end weight (wet weight) was recorded and the absorbency potential was calculated.

Retention post compression was also measured. Following submergence of a sample in the test solution as described above, a weight representative of 40 mm/Mg pressure was applied to the sample for five minutes. The retention of fluid in the sample was calculated.

Test 2:

A known area of each of samples 'C-EtO', 'C-Gamma', 'C-Non-sterile', 'D-EtO', 'D-Gamma' and 'D-Non-sterile', was weighed (dry weight), followed by submersion in the test solution over different time periods of 10 minutes, 1 hour, 24 hours, 48 hours and 5 days. The end weight (wet weight) was recorded and the absorbency potential calculated.

Results

Figure 2:
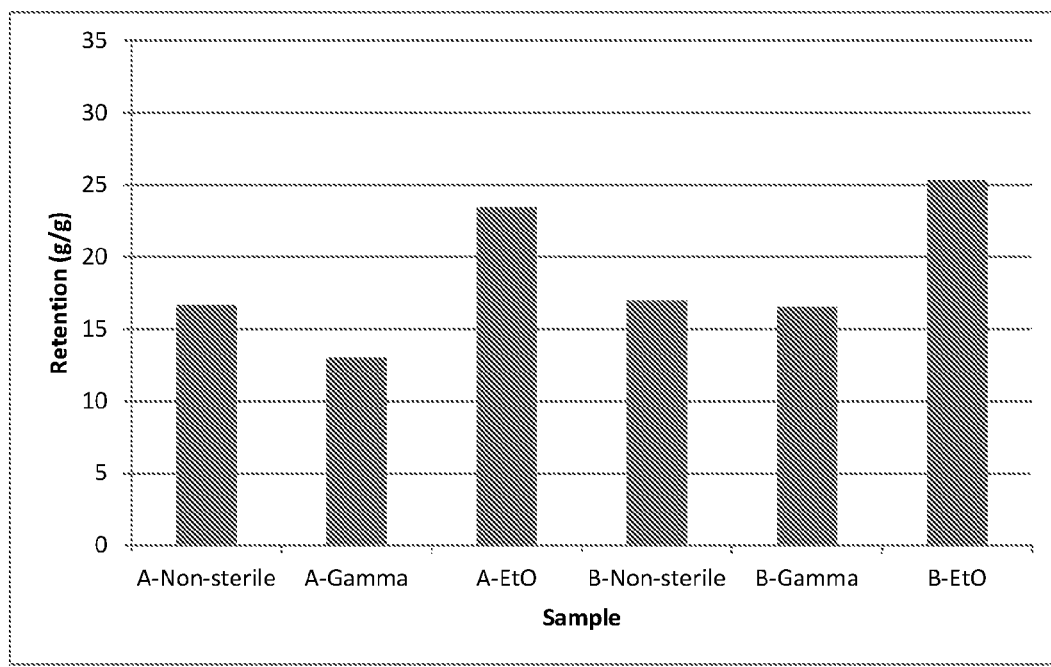
FIG. 2: is a graphical representation showing post-compression fluid retention for a sample wound care device exposed to different sterilisation methods.

The results of Test 1 are shown in Table 3 and FIGS. 1 and 2.

TABLE 3

Absorbency and retention results for Test 1

| Sample reference | Sterilisation | Absorbency (g/g) | Retention (g/g) |
|---|---|---|---|
| A | Non-sterile | 22.48 | 16.64 |
|   | Gamma | 22.97 | 13.00 |
|   | EtO | 30.09 | 23.47 |
| B | Non-sterile | 24.00 | 17.00 |
|   | Gamma | 23.74 | 16.54 |
|   | EtO | 30.82 | 25.31 |

Referring to FIG. 1, it is apparent that the absorbency of sample 'A-EtO' is higher than that of samples 'A-Gamma' and 'A-Non-sterile' and the absorbency of sample B-EtO' is higher than that of samples 'B-Gamma' and 'B-Non-sterile'.

Referring to FIG. 2, it is apparent that the post compression fluid retention of sample 'A-EtO' is higher than that of samples 'A-Gamma' and 'A-Non-sterile' and the retention of sample B-EtO' is higher than that of samples 'B-Gamma' and 'B-Non-sterile'.

Figure 3:
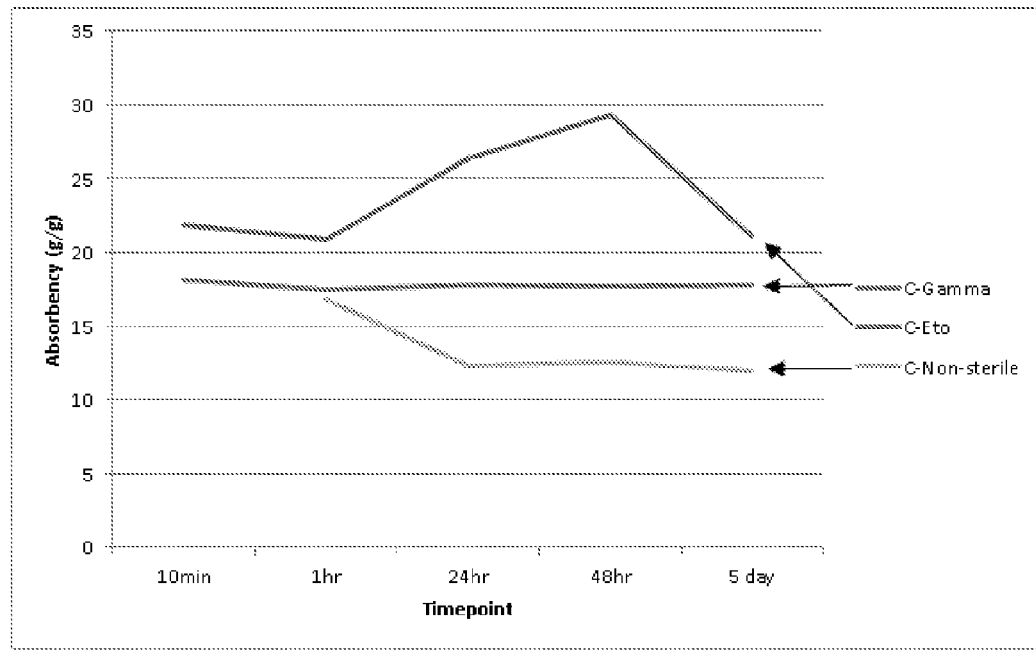
FIG. 3: is a graphical representation showing absorbency over time for a sample wound care device in accordance with an embodiment of the present invention exposed to different sterilisation methods.
Figure 4:
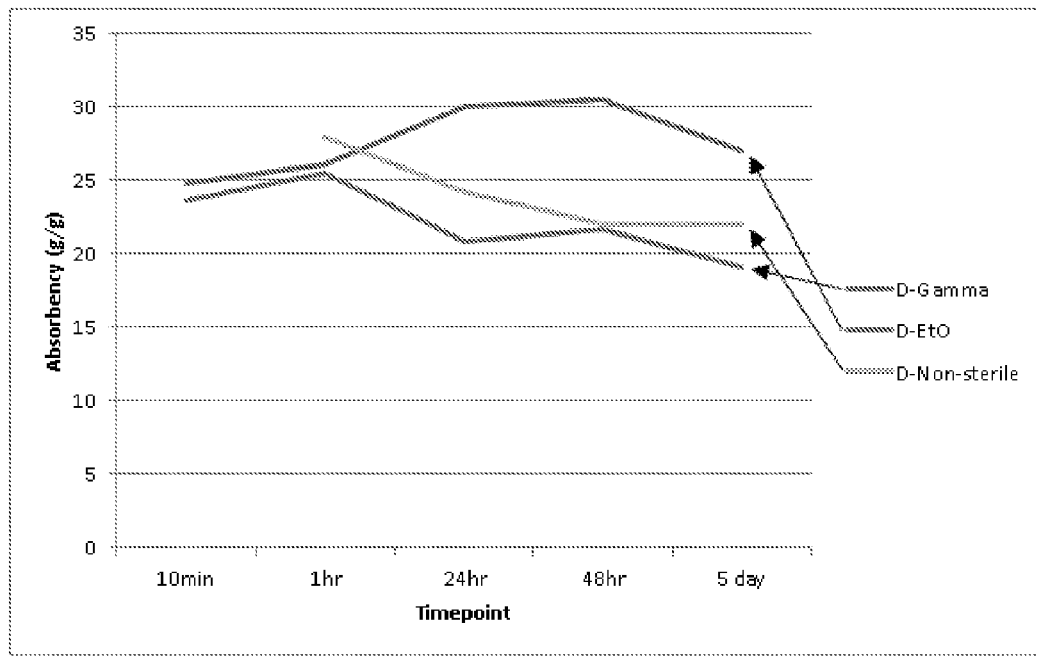
FIG. 4: is a graphical representation showing absorbency over time for a further sample wound care device in accordance with an embodiment of the present invention exposed to different sterilisation methods.

The data presented demonstrates that the performance of a wound care device comprising a first material and an acidic substance is dependent on the sterilisation technique used, with samples exposed to ethylene oxide showing improved absorbency and fluid retention post-compression The results of Test 2 are shown in Table 4 and FIGS. 3 and 4.

TABLE 4

Absorbency results for Test 2 (NT = Not tested)

| | | Absorbency (g/g)/time point | | | | |
|---|---|---|---|---|---|---|
| Sample reference | Sterilisation | 10 min | 1 hr | 24 hr | 48 hr | 5 day |
| C | Gamma | 18.14 | 17.49 | 17.85 | 17.68 | 17.79 |
|   | EtO | 21.82 | 20.93 | 26.34 | 29.38 | 21.14 |
|   | Non-sterile | NT | 16.8 | 12.3 | 12.5 | 12.0 |
| D | Gamma | 23.68 | 25.45 | 20.80 | 21.63 | 19.06 |
|   | EtO | 24.82 | 26.10 | 30.04 | 30.45 | 27.06 |
|   | Non-sterile | NT | 27.9 | 24.2 | 22.0 | 22.0 |

Referring to FIG. 3, it is apparent that the absorbency of sample 'C-EtO' is higher than that of samples 'C-Gamma' and 'C-Non-sterile'.

Referring to FIG. 4, it is again shown that the absorbency of sample 'D-EtO' is higher than that of samples 'D-Gamma' and 'D-Non-sterile'.

The data presented demonstrates that the performance of a wound care device comprising a first material and a second material having an acid associated therewith is dependent on the sterilisation technique used.

The wound care device is designed to absorb fluid and create a gel to maintain a moist wound environment.

The results from FIGS. 3 and 4 also show that the initial absorbency of a wound care device exposed to ethylene oxide is higher than that of the wound care device exposed to gamma irradiation, or no sterilisation at all.

In the prepared samples C and D, it has also been discovered that when the lactic acid level is between 25-30% of the cellulose fibre, the wound care device exposed to ethylene oxide gels and maintains its structure over the five-day test period, having an absorbency greater than the corresponding gamma irradiated wound care device and the non-sterile wound care device.

It is of course to be understood that the present invention is not intended to be restricted to the foregoing examples which are described by way of example only.

The invention claimed is:

1. A wound care device obtainable by exposing to ethylene oxide an intermediate device, the intermediate device comprising a first material comprising chitosan, a partially de-acetylated chitin and/or a chitosan derivative in the form of fibres, particles, granules, flakes, powder, or a combination of two or more of the aforesaid, and an acidic substance absorbed in or coated on a second material without permanent bonding occurring, which first material does not gel when exposed to a wound fluid but does gel when brought together with the acidic substance and exposed to a wound fluid, wherein the first material and the acidic substance of the intermediate device do not react with each other prior to exposing the intermediate device to ethylene oxide.

2. A wound care device as claimed in claim 1, wherein the chitosan is in the form of fibres.

3. A wound care device as claimed in claim 1, wherein the acidic substance comprises one or more acids.

4. A wound care device as claimed in claim 3, wherein the one or more acids are selected from any of the following: formic, acetic, halogen acetic acids, ascorbic, hydrochloric, sulphuric, propanoic, propenoic, lactic, succinic, acrylic, glyoxylic, pyruvic or a hydroxy propionic/butanoic acid, or combinations thereof.

5. A wound care device as claimed in claim 1, wherein the second material and the acidic substance do not react with each other prior to exposing the intermediate device to ethylene oxide.

6. A wound care device as claimed in claim 1, wherein the second material is selected from any of the following: cellulose, cellulose derivatives, cotton, alginate, viscose, polypropylene, polyethylene or combinations thereof.

7. A method of using the wound care device of claim 1 by applying the wound care device to a physiological target site to absorb a discharge of a bodily fluid.

8. A wound care device as claimed in claim 1, wherein the wound fluid is a water-containing fluid selected from the group consisting of water, saline, wound exudates, blood, and combinations thereof.

* * * * *